United States Patent
Peltola et al.

(10) Patent No.: US 10,315,045 B2
(45) Date of Patent: Jun. 11, 2019

(54) METHOD AND APPARATUS FOR USING A DESIGNATED PATIENT STRUCTURE AS AN AREA TO BE MASKED FROM RADIATION

(71) Applicant: Varian Medical Systems International AG, Zug (CH)

(72) Inventors: Jarkko Peltola, Tuusula (FI); Janne Nord, Espoo (FI); Maria Isabel Cordero Marcos, Espoo (FI)

(73) Assignee: Varian Medical Systems International AG, Steinhausen (CH)

( * ) Notice: Subject to any disclaimer, the term of this patent is extended or adjusted under 35 U.S.C. 154(b) by 526 days.

(21) Appl. No.: 14/040,095

(22) Filed: Sep. 27, 2013

(65) Prior Publication Data
US 2014/0275702 A1    Sep. 18, 2014

Related U.S. Application Data

(60) Provisional application No. 61/784,110, filed on Mar. 14, 2013.

(51) Int. Cl.
*A61N 5/10* (2006.01)

(52) U.S. Cl.
CPC ......... *A61N 5/1001* (2013.01); *A61N 5/1031* (2013.01); *A61N 5/1038* (2013.01); *A61N 5/1047* (2013.01); *A61N 5/1048* (2013.01); *A61N 5/1064* (2013.01)

(58) Field of Classification Search
CPC ........ A61N 5/10; A61N 5/103; A61N 5/1036; A61N 5/1042–5/1045; A61N 5/1047; A61N 5/1048; A61N 5/1064; A61N 5/1065; A61N 5/1071; G21K 1/02; G21K 1/025; G21K 1/04; G21K 1/046
See application file for complete search history.

(56) References Cited

U.S. PATENT DOCUMENTS

2006/0274885 A1\* 12/2006 Wang et al. .................... 378/65

\* cited by examiner

*Primary Examiner* — Carrie R Dorna
(74) *Attorney, Agent, or Firm* — Fitch, Even, Tabin & Flannery LLP

(57) ABSTRACT

A control circuit provides a user with an opportunity to designate one or more patient structures for a particular patient that are to be protected from radiation. When optimizing a radiation-treatment plan for that patient, then, the control circuit uses the designated patient structure(s) as an area to be masked from radiation during administration of the radiation-treatment plan. By one approach the aforementioned opportunity to designate patient structures as being designated patient structures comprises providing the user with an opportunity to so designate patient structures via a display. The aforementioned masking can be accomplished as desired including by appropriate use of a multi-leaf collimator.

12 Claims, 3 Drawing Sheets

METHOD AND APPARATUS FOR USING A DESIGNATED PATIENT STRUCTURE AS AN AREA TO BE MASKED FROM RADIATION

RELATED APPLICATION(S)

This application claims the benefit of U.S. Provisional application No. 61/784,110, filed Mar. 14, 2013, which is incorporated by reference in its entirety herein.

TECHNICAL FIELD

This invention relates generally to the therapeutic irradiation of a patient's target volume.

BACKGROUND

The use of radiation to treat medical conditions comprises a known area of prior art endeavor. For example, radiation therapy comprises an important component of many treatment plans for reducing or eliminating unwanted tumors. Unfortunately, applied radiation does not inherently discriminate between unwanted areas and adjacent healthy tissues, organs, or the like that are desired or even critical to continued survival of the patient. As a result, radiation is ordinarily applied in a carefully administered manner to at least attempt to restrict the radiation to a given target volume.

Treatment plans typically serve to specify any number of operating parameters as pertain to the administration of such treatment with respect to a given patient. Such treatment plans are often optimized prior to use. (As used herein, "optimization" will be understood to refer to improving upon a candidate treatment plan without necessarily ensuring that the optimized result is, in fact, the singular best solution.) Many optimization approaches use an automated incremental methodology where various optimization results are calculated and tested in turn using a variety of automatically-modified (i.e., "incremented") treatment plan optimization parameters.

Many treatment plans provide for exposing the target volume to radiation from a number of different angles. Arc therapy, for example, comprises one such approach. In such a case it often becomes useful or necessary to also adjust various mechanical components (such as, for example, multi-leaf collimators) of the treatment system when moving the radiation source with respect to the target volume. A radiation-treatment plan therefore often provides information regarding useful or necessary adjustments to various mechanical components of the treatment system during such a treatment.

Not infrequently one or more of the available angles includes in the beam's-eye view patient structure that should be protected from radiation. When such patient structure partially overlies (in the beam's-eye view) the patient target volume, a tried-and-true approach to planning the treatment session calls for directing no radiation towards the volume target from such angles. Unfortunately, such an approach can result in effectively losing a considerable number of exposure angles and that circumstance, in turn, can undercut the very reason to use an arc-therapy approach for a particular patient in that using only a reduced number of exposure angles inherently increases the amount of radiation being delivered to at least some non-targeted tissue.

BRIEF DESCRIPTION OF THE DRAWINGS

The above needs are at least partially met through provision of the method and apparatus for using a designated patient structure as an area to be masked from radiation described in the following detailed description, particularly when studied in conjunction with the drawings, wherein.

Elements in the figures are illustrated for simplicity and clarity and have not necessarily been drawn to scale. For example, the dimensions and/or relative positioning of some of the elements in the figures may be exaggerated relative to other elements to help to improve understanding of various embodiments of the present invention. Also, common but well-understood elements that are useful or necessary in a commercially feasible embodiment are often not depicted in order to facilitate a less obstructed view of these various embodiments of the present invention. Certain actions and/or steps may be described or depicted in a particular order of occurrence while those skilled in the art will understand that such specificity with respect to sequence is not actually required. The terms and expressions used herein have the ordinary technical meaning as is accorded to such terms and expressions by persons skilled in the technical field as set forth above except where different specific meanings have otherwise been set forth herein.

DETAILED DESCRIPTION

Generally speaking, pursuant to these various embodiments a control circuit provides a user with an opportunity to designate one or more patient structures for a particular patient that is to be protected from radiation. When optimizing a radiation-treatment plan for that patient, then, the control circuit uses the designated patient structure(s) as an area to be masked from radiation during administration of the radiation-treatment plan. By one approach the aforementioned opportunity to designate patient structures as being designated patient structures comprises providing the user with an opportunity to so designate patient structures via a display. The aforementioned masking can be accomplished as desired including by appropriate use of a multi-leaf collimator.

So configured, an arc field where a target volume is partially disposed behind a troublesome patient structure (such as a structure, for example, that will absorb relatively more radiation and thereby deny the desired dosing of part of the target volume) can nevertheless still be used to deliver radiation to the available "visible" target volume by masking the foreground patient structure from receiving radiation. Accordingly, more angles can be used to at least some good effect and the amount of radiation delivered to non-targeted tissues can generally be lowered as compared to many prior art approaches in these regards.

Figure 1:
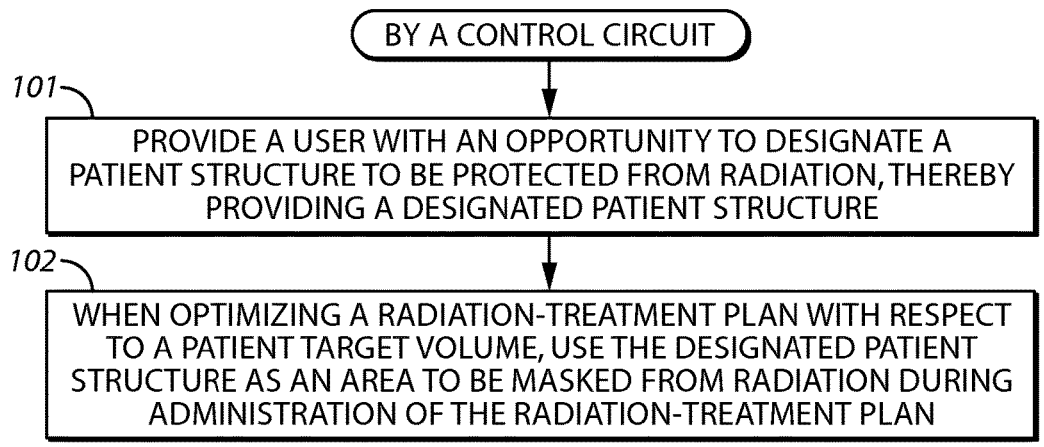
FIG. 1 comprises a flow diagram as configured in accordance with various embodiments of the invention.

These and other benefits may become clearer upon making a thorough review and study of the following detailed description. Referring now to the drawings, and in particular to FIG. 1, an illustrative process 100 that is compatible with many of these teachings will now be presented. For the sake of an illustrative example the following description presumes that a control circuit of choice carries out this process 100

Figure 2:
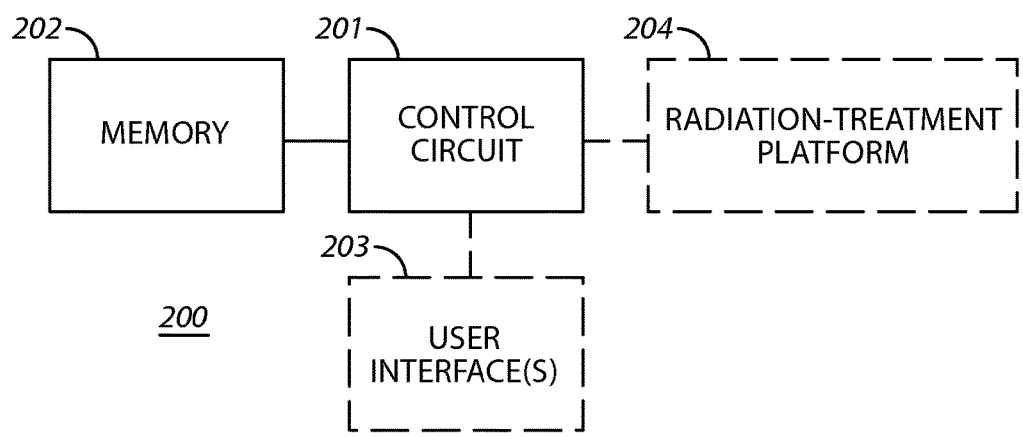
FIG. 2 comprises a block diagram as configured in accordance with various embodiments of the invention.

Referring momentarily to the illustrative example shown in FIG. 2, an enabling apparatus 200 includes a control circuit 201 that operably couples to a memory 202 and to an optional user interface 203. Such a control circuit 201 can comprise a fixed-purpose hard-wired platform or can comprise a partially or wholly programmable platform. These architectural options are well known and understood in the art and require no further description here. This control circuit 201 is configured (for example, by using corresponding programming as will be well understood by those skilled in the art) to carry out one or more of the steps, actions, and/or functions described herein.

The memory 202 may be integral to the control circuit 201 or can be physically discrete (in whole or in part) from the control circuit 201 as desired. This memory 202 can also be local with respect to the control circuit 201 (where, for example, both share a common circuit board, chassis, power supply, and/or housing) or can be partially or wholly remote with respect to the control circuit 201 (where, for example, the memory 202 is physically located in another facility, metropolitan area, or even country as compared to the control circuit 201).

This memory 202 can serve, for example, to non-transitorily store the computer instructions that, when executed by the control circuit 201, cause the control circuit 201 to behave as described herein. (As used herein, this reference to "non-transitorily" will be understood to refer to a non-ephemeral state for the stored contents (and hence excludes when the stored contents merely constitute signals or waves) rather than volatility of the storage media itself and hence includes both non-volatile memory (such as read-only memory (ROM) as well as volatile memory (such as an erasable programmable read-only memory (EPROM).)

The user interface 203 can comprise any of a variety of user-input mechanisms (such as, but not limited to, keyboards and keypads, cursor-control devices, touch-sensitive displays, speech-recognition interfaces, gesture-recognition interfaces, and so forth) and/or user-output mechanisms (such as, but not limited to, visual displays, audio transducers, printers, and so forth) to facilitate receiving information and/or instructions from a user and/or providing information to a user.

These teachings will also accommodate operably coupling the control circuit 201 to a radiation-treatment platform 204 (such as, by way of a non-limiting illustrative example, an arc-therapy radiation-treatment platform) of choice. So configured, the control circuit 201 can delivered the optimized radiation-therapy treatment plan to that platform 204 for use in treating the corresponding patient.

Such an apparatus 200 may be comprised of a plurality of physically distinct elements as is suggested by the illustration shown in FIG. 2. It is also possible, however, to view this illustration as comprising a logical view, in which case one or more of these elements can be enabled and realized via a shared platform. It will also be understood that such a shared platform may comprise a wholly or at least partially programmable platform as are known in the art.

Referring now to both FIGS. 1 and 2, at block 101 this process 100 provides a user with an opportunity to designate a patient structure (or structures) to be protected from radiation. The teachings will accommodate a variety of patient structures including both natural biological structures as well as implanted man-made artifacts such a heart pacemakers.

Figure 3:
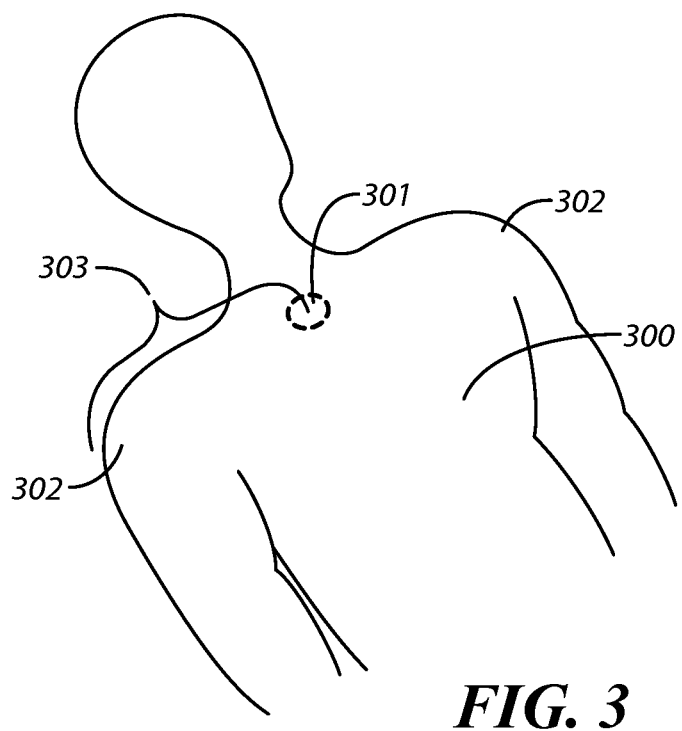
FIG. 3 comprises a schematic perspective view as configured in accordance with various embodiments of the invention.

Referring to the illustrative example provided in FIG. 3, a given patient 300 has a target volume 301 located between their shoulders 302. Such a circumstance is known to present problematic issues when irradiating the target volume 301 from the side and in-line with the patient's shoulders 302. In particular, and as denoted by reference numeral 303, there is a considerable distance through the patient that a radiation beam must traverse before reaching the target volume 301 (and especially as compared, for example, to exposing the target volume 301 from directly above the patient's body). It is just such a circumstance that prompts many prior art approaches to simply eschew directing any radiation towards the target volume from such an angle.

Figure 4:
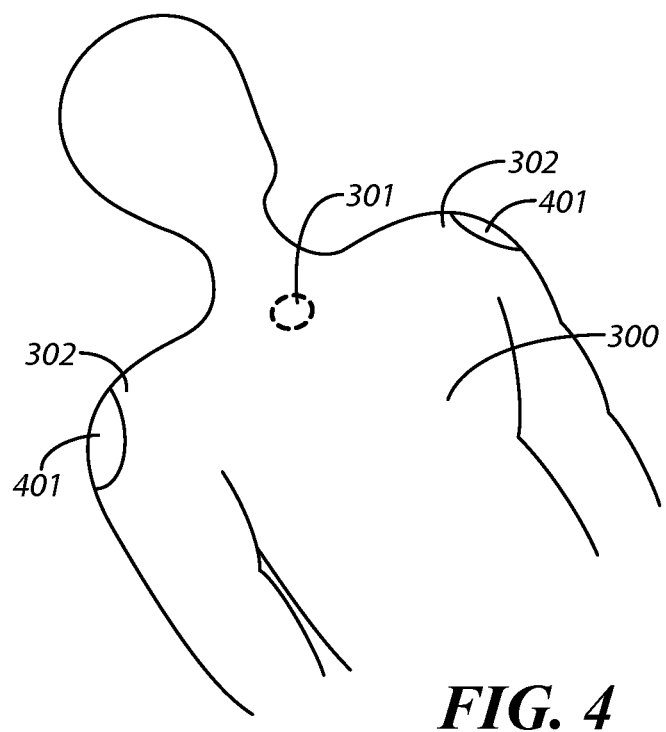
FIG. 4 comprises a schematic perspective view as configured in accordance with various embodiments of the invention.

FIG. 4 continues with the example begun in FIG. 3 and includes areas denoted by reference numeral 401 where the user has designated the aforementioned patient structures. In particular, these designated areas 401 comprise lateral exterior aspects of both shoulders 302.

There are various ways to present such an opportunity. By one approach, the aforementioned user interface 203 can include a display that presents a view (or views) of the patient 300. The aforementioned opportunity can then comprise letting the user visually indicate the part (or parts) of the patient 300 that are to be designated as described. This could comprise, for example, providing the user with the ability to digitally "paint" the corresponding patient structures using any of a variety of known techniques in these regards.

At block 102 this process 100 then provides for having the control circuit 201 use the designated patient structure(s) as an area(s) to be masked from radiation during administration of a radiation-treatment plan when optimizing that plan. Masking, in turn, can be accomplished, at least in part, by planned use of one or more multi-leaf collimators. Multi-leaf collimators are comprised of a plurality of individual parts (known as "leaves") that are formed of a high atomic numbered material (such as tungsten) that can move independently in and out of the path of the radiation-therapy beam in order to selectively block (and hence shape) the beam. These leaves are typically utilized to form one or more apertures through which a radiation beam can pass without attenuation.

Figure 5:
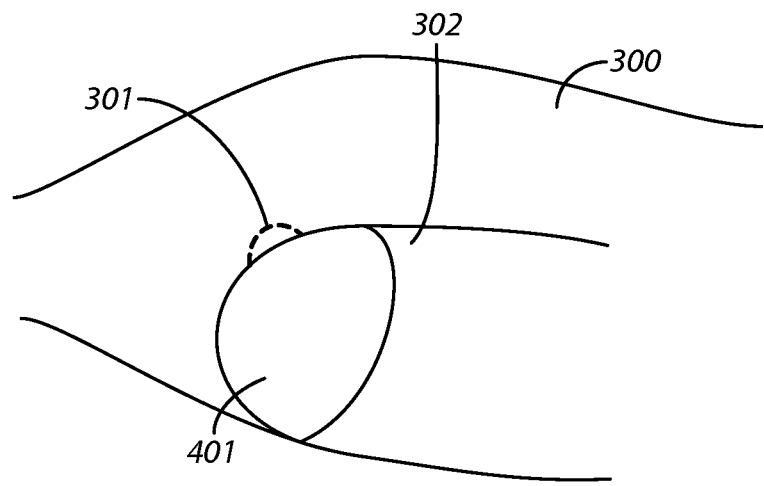
FIG. 5 comprises a schematic side elevational view as configured in accordance with various embodiments of the invention.
Figure 6:
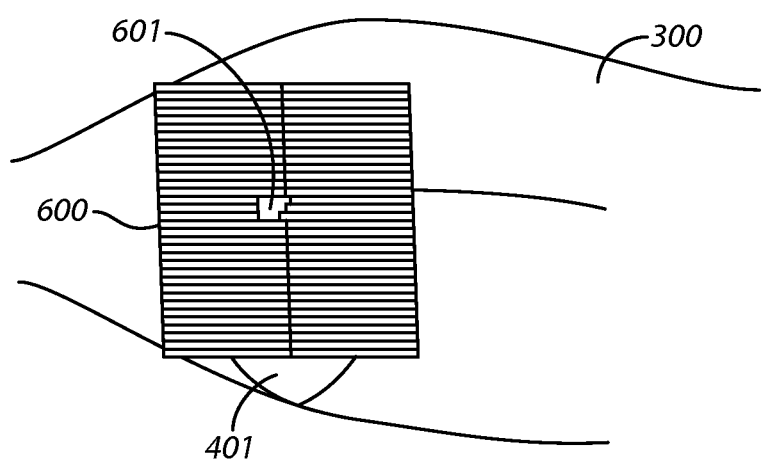
FIG. 6 comprises a schematic side elevational view as configured in accordance with various embodiments of the invention.

FIGS. 5 and 6 offer an illustrative (but non-limiting) example in these regards. FIG. 5 provides a sideways view of the patient's 300 upper torso. From this angle the patient's shoulder 302 is partially overlapping with the target volume 301 (and, in particular, lies in the foreground between the target volume 301 and the source of radiation). Instead of avoiding any irradiation of the target volume 301 from this angle, and referring now to FIG. 6, a multi-leaf collimator 600 is configured to mask the aforementioned designated patient structure 401 (i.e., the patient's shoulder 302) and, by way of an appropriately sized, located, and oriented aperture 601 that essentially matches that part of the target volume 301 that is not also in-line with the designated patient structure 401, permit some radiation to reach the target volume 301. So configured, while radiation provided from this angle will not irradiate the entire target volume 301, at least part of the target volume 301 is irradiated and without collateral irradiation of the designated patient structure 401.

Such interplay between a designated patient structure 401 and the target volume 301 will typically change from one field to another as the radiation source moves around the treatment arc. In many fields there may be no meaningful interplay at all and in such cases the multi-leaf collimator 600 can be employed in a traditional manner to simply mask non-targeted tissues that flank the target volume 301. In other cases, where for example the designated patient structure is disposed at least partially between the radiation source and the target volume 301, the multi-leaf collimator 600 can be configured to mask not only the flanking non-targeted tissues but that part of the designated patient structure that overlies the target volume 301 as well.

Accordingly, the described use of the designated patient structure as an area to be masked from radiation during administration of the radiation-treatment plan can occur on a field-by-field basis for a given radiation-treatment session (and particularly when, for example, the radiation-treatment session comprises an arc-based radiation-treatment session).

So configured, by permitting a user to identify certain patient structures as areas to be avoiding when irradiating a patient's target volume, a masking apparatus (such as a multi-leaf collimator) can be used to not only mask non-targeted tissues to the sides of the target volume but to also provide for masking portions of the target volume itself when the designated patient structure is positioned between the target volume and the source of radiation. This approach permits at least some value to be leveraged from gantry angles that were previously passed without use and to thereby help to reduce the amount of unwanted collateral radiation that at least some untargeted tissues will receive.

Those skilled in the art will recognize that a wide variety of modifications, alterations, and combinations can be made with respect to the above described embodiments without departing from the scope of the invention, and that such modifications, alterations, and combinations are to be viewed as being within the ambit of the inventive concept.

What is claimed is:

1. An apparatus comprising:
    a control circuit configured to:
        provide a user with an opportunity to designate a patient structure to be protected from radiation when the designated patient structure overlies a patient target volume in a particular radiation treatment angle, thereby providing a designated patient structure;
        when optimizing a radiation-treatment plan with respect to the patient target volume, using the designated patient structure as an area to be masked from radiation by at least one multi-leaf collimator during administration of the radiation-treatment plan when the designated patient structure is positioned between the patient target volume and a source of radiation;
    a radiation treatment platform operably coupled to the control circuit and configured to deliver the radiation-treatment plan as optimized to a patient.

2. The apparatus of claim 1 further comprising:
    a display that operably couples to the control circuit;
    wherein the control circuit is configured to provide the user with the opportunity to designate the patient structure to be protected from radiation via the display.

3. The apparatus of claim 1 wherein the control circuit is configured to use the designated patient structure as an area to be masked from radiation during administration of the radiation-treatment plan such that at least some part of the patient target volume is irradiated in a given field notwithstanding masking of the designated patient structure.

4. The apparatus of claim 1 wherein the control circuit is configured to use the designated patient structure as an area to be masked from radiation during administration of the radiation-treatment plan on a field-by-field basis for a given radiation-treatment session.

5. The apparatus of claim 4 wherein the given radiation-treatment session comprises an arc-based radiation-treatment session.

6. The apparatus of claim 1 wherein the control circuit is configured to use the designated patient structure as an area to be masked from radiation during administration of the radiation-treatment plan only when the designated patient structure is positioned between the patient target volume and the source of the radiation.

7. A method comprising:
    by a control circuit:
        providing a user with an opportunity to designate a patient structure to be protected from radiation when the designated patient structure overlies a patient target volume in a particular radiation treatment angle, thereby providing a designated patient structure;
        when optimizing a radiation-treatment plan with respect to the patient target volume, using the designated patient structure as an area to be masked from radiation by at least one multi-leaf collimator during administration of the radiation-treatment plan when the designated patient structure is positioned between the patient target volume and a source of radiation;
    delivering the radiation-treatment plan as optimized to a patient using a radiation-treatment platform.

8. The method of claim 7 wherein providing the user with the opportunity comprises providing the user with the opportunity to designate the patient structure to be protected from radiation via a display.

9. The method of claim 7 wherein using the designated patient structure as an area to be masked from radiation during administration of the radiation-treatment plan comprises using the designated patient structure as an area to be masked from radiation during administration of the radiation-treatment plan such that at least some part of the patient target volume is irradiated in a given field notwithstanding masking of the designated patient structure.

10. The method of claim 7 wherein using the designated patient structure as an area to be masked from radiation during administration of the radiation-treatment plan comprises using the designated patient structure as an area to be masked from radiation during administration of the radiation-treatment plan on a field-by-field basis for a given radiation-treatment session.

11. The method of claim 10 wherein the given radiation-treatment session comprises an arc-based radiation-treatment session.

12. The method of claim 7 wherein using the designated patient structure as an area to be masked from radiation during administration of the radiation-treatment plan comprises using the designated patient structure as an area to be masked from radiation during administration of the radiation-treatment plan only when the designated patient structure is positioned between the patient target volume and the source of the radiation.

* * * * *